(12) United States Patent
Shelton et al.

(10) Patent No.: US 12,023,096 B2
(45) Date of Patent: Jul. 2, 2024

(54) MEDICAL LASER APPARATUS AND SYSTEM

(71) Applicant: GYRUS ACMI, INC., Southborough, MA (US)

(72) Inventors: Kurt G. Shelton, Bedford, MA (US); Masayasu Chida, Tokyo (JP)

(73) Assignee: Gyrus ACMI, Inc., Westborough, MA (US)

( * ) Notice: Subject to any disclaimer, the term of this patent is extended or adjusted under 35 U.S.C. 154(b) by 823 days.

(21) Appl. No.: 16/968,800

(22) PCT Filed: Feb. 8, 2019

(86) PCT No.: PCT/US2019/017153
§ 371 (c)(1),
(2) Date: Aug. 10, 2020

(87) PCT Pub. No.: WO2019/157247
PCT Pub. Date: Aug. 15, 2019

(65) Prior Publication Data
US 2021/0045811 A1    Feb. 18, 2021

Related U.S. Application Data

(60) Provisional application No. 62/628,513, filed on Feb. 9, 2018.

(51) Int. Cl.
*A61B 1/00*     (2006.01)
*A61B 1/015*    (2006.01)
(Continued)

(52) U.S. Cl.
CPC .......... *A61B 18/26* (2013.01); *A61B 1/00006* (2013.01); *A61B 1/00055* (2013.01);
(Continued)

(58) Field of Classification Search
CPC . A61B 18/26; A61B 1/00006; A61B 1/00055; A61B 1/00087; A61B 1/015;
(Continued)

(56) References Cited

U.S. PATENT DOCUMENTS 4,971,034 A    11/1990  Doi et al.
5,785,702 A     7/1998  Murphy-Chutorian et al.
(Continued)

FOREIGN PATENT DOCUMENTS

CA    2734120 C    9/2016
CN    1249162 A    4/2000
(Continued)

OTHER PUBLICATIONS

"European Application Serial No. 19750915.1, Extended European Search Report dated Nov. 22, 2021", 8 pgs.
(Continued)

*Primary Examiner* — Timothy J Neal
*Assistant Examiner* — James Edward Boice
(74) *Attorney, Agent, or Firm* — Schwegman Lundberg & Woessner, P.A.

(57) ABSTRACT

A medical laser apparatus, including: an energy guide; a first energy source configured to generate energy for treating a target tissue through the energy guide; a second energy source configured to emit first and second aiming beams to a target tissue through the energy guide, the second aiming beam having at least one characteristic different from the first aiming beam; and a controller comprising hardware, the controller being configured to: receive a signal indicating an illumination mode from at least two illumination modes used by an endoscope to illuminate the target tissue; and control the second energy source to output the first or second aiming beam based on the indicated illumination mode.

23 Claims, 4 Drawing Sheets

(51) Int. Cl.
*A61B 1/018* (2006.01)
*A61B 1/06* (2006.01)
*A61B 1/12* (2006.01)
*A61B 1/307* (2006.01)
*A61B 1/31* (2006.01)
*A61B 18/24* (2006.01)
*A61B 18/26* (2006.01)
*A61M 1/00* (2006.01)
*H01S 3/067* (2006.01)
*A61B 1/05* (2006.01)
*A61B 17/3207* (2006.01)
*A61B 18/00* (2006.01)
*H01S 3/16* (2006.01)

(52) U.S. Cl.
CPC .......... *A61B 1/00087* (2013.01); *A61B 1/015* (2013.01); *A61B 1/018* (2013.01); *A61B 1/06* (2013.01); *A61B 1/126* (2013.01); *A61B 1/307* (2013.01); *A61B 1/31* (2013.01); *A61B 18/24* (2013.01); *A61M 1/74* (2021.05); *A61M 1/77* (2021.05); *H01S 3/06716* (2013.01); *A61B 1/00045* (2013.01); *A61B 1/00105* (2013.01); *A61B 1/05* (2013.01); *A61B 17/320783* (2013.01); *A61B 2018/00482* (2013.01); *A61B 2018/00505* (2013.01); *A61B 2018/00511* (2013.01); *A61B 2018/00559* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00773* (2013.01); *A61B 2018/00982* (2013.01); *A61B 2217/005* (2013.01); *A61B 2217/007* (2013.01); *A61B 2562/0247* (2013.01); *A61M 2205/3334* (2013.01); *A61M 2205/3344* (2013.01); *H01S 3/1616* (2013.01)

(58) Field of Classification Search
CPC ........... A61B 1/018; A61B 1/06; A61B 1/126; A61B 1/307; A61B 1/31; A61B 18/24; A61B 1/00045; A61B 1/00105; A61B 1/05; A61B 17/320783; A61B 2018/00482; A61B 2018/00505; A61B 2018/00511; A61B 2018/00559; A61B 2018/00672; A61B 2018/00678; A61B 2018/00696; A61B 2018/00982; A61B 2217/005; A61B 2217/007; A61B 2562/0247; A61M 1/77; A61M 1/74; A61M 2205/3334; A61M 2205/3344; H01S 3/06716; H01S 3/1616
USPC ........................................................ 600/108
See application file for complete search history.

(56) References Cited

U.S. PATENT DOCUMENTS

| | | |
|---|---|---|
| 5,931,834 A | 8/1999 | Murphy-Chutorian et al. |
| 6,156,049 A | 12/2000 | Lovato et al. |
| 6,527,716 B1 | 3/2003 | Eppstein |
| 8,109,872 B2 | 2/2012 | Kennedy, II et al. |
| 9,259,231 B2 | 2/2016 | Navve et al. |
| 9,308,315 B2 | 4/2016 | Stubkjaer et al. |
| 9,597,160 B1 | 3/2017 | Gregg et al. |
| 9,907,563 B2 | 3/2018 | Germain et al. |
| 10,201,382 B2 | 2/2019 | Wiener et al. |
| 10,441,345 B2 | 10/2019 | Aldridge et al. |
| 2003/0036751 A1 | 2/2003 | Anderson et al. |
| 2004/0229295 A1 | 11/2004 | Marchitto et al. |
| 2005/0222535 A1 | 10/2005 | Uesugi et al. |
| 2006/0047185 A1 | 3/2006 | Shener et al. |
| 2006/0264995 A1 | 11/2006 | Fanton et al. |
| 2008/0154185 A1 | 6/2008 | Blight |
| 2008/0300662 A1 | 12/2008 | Taylor |
| 2009/0058996 A1* | 3/2009 | Mitsuhashi ........ A61B 1/00016 348/E7.085 |
| 2009/0156900 A1 | 6/2009 | Robertson |
| 2010/0004510 A1 | 1/2010 | Kuroshima |
| 2010/0049119 A1 | 2/2010 | Norman et al. |
| 2010/0076304 A1 | 3/2010 | Teramura |
| 2011/0082449 A1 | 4/2011 | Melsky et al. |
| 2011/0237880 A1 | 9/2011 | Hamel et al. |
| 2012/0116168 A1 | 5/2012 | Moellstam et al. |
| 2013/0303852 A1 | 11/2013 | Hiraga et al. |
| 2015/0119645 A1 | 4/2015 | Baldwin |
| 2015/0133728 A1 | 5/2015 | Finkman et al. |
| 2015/0216394 A1 | 8/2015 | Toyoda |
| 2015/0230864 A1 | 8/2015 | Xuan et al. |
| 2015/0320303 A1 | 11/2015 | Kawase |
| 2015/0320433 A1 | 11/2015 | Navve et al. |
| 2015/0342682 A1 | 12/2015 | Bowe |
| 2016/0022126 A1 | 1/2016 | Ramesh et al. |
| 2016/0022289 A1 | 1/2016 | Wan |
| 2016/0135894 A1 | 5/2016 | Finkman et al. |
| 2016/0157954 A1 | 6/2016 | Sagon et al. |
| 2016/0206805 A1 | 7/2016 | Hassidov et al. |
| 2016/0250075 A1 | 9/2016 | Kawai et al. |
| 2017/0112572 A1 | 4/2017 | Shazly et al. |
| 2017/0215989 A1 | 8/2017 | Gregg et al. |
| 2017/0220754 A1 | 8/2017 | Harrah et al. |
| 2017/0325890 A1 | 11/2017 | Chia et al. |
| 2018/0084980 A1* | 3/2018 | Watanabe ............ A61B 1/0655 |
| 2018/0168439 A1 | 6/2018 | Hibbs et al. |
| 2018/0289394 A1 | 10/2018 | Shah |
| 2018/0325622 A1 | 11/2018 | Groves, Jr. et al. |
| 2019/0008545 A1 | 1/2019 | Stulen et al. |
| 2019/0134279 A1 | 5/2019 | Benamou et al. |
| 2019/0247566 A1 | 8/2019 | Hassidov et al. |
| 2019/0282073 A1 | 9/2019 | Truckai |
| 2020/0000522 A1 | 1/2020 | Chia et al. |
| 2020/0187761 A1 | 6/2020 | Shelton |
| 2020/0187768 A1 | 6/2020 | Shelton et al. |
| 2020/0330157 A1 | 10/2020 | Junger et al. |
| 2020/0405130 A9 | 12/2020 | Shelton |
| 2021/0045812 A1 | 2/2021 | Talbot et al. |
| 2021/0220529 A1 | 7/2021 | Wang |
| 2021/0244267 A1 | 8/2021 | Shtul et al. |

FOREIGN PATENT DOCUMENTS

| | | |
|---|---|---|
| CN | 101273915 A | 10/2008 |
| CN | 104619281 A | 5/2015 |
| CN | 106232037 A | 12/2016 |
| CN | 106456368 A | 2/2017 |
| CN | 111683580 A | 9/2020 |
| CN | 111683617 A | 9/2020 |
| CN | 115175626 A | 10/2022 |
| CN | 115334982 A | 11/2022 |
| DE | 112021001260 T5 | 12/2022 |
| DE | 112021001396 T5 | 12/2022 |
| EP | 0048410 A1 | 3/1982 |
| EP | 1086674 A1 | 3/2001 |
| EP | 3429453 A1 | 1/2019 |
| JP | S5971736 A | 4/1984 |
| JP | H08201026 A | 8/1996 |
| JP | 2003210485 A | 7/2003 |
| JP | 2007244679 A | 9/2007 |
| JP | 2010075314 A | 4/2010 |
| JP | 2016533830 A | 11/2016 |
| JP | 2017500172 A | 1/2017 |
| JP | 2017522058 A | 8/2017 |
| JP | 7374911 B2 | 10/2023 |
| WO | WO-2011032165 A2 | 3/2011 |
| WO | WO-2013099507 A1 | 7/2013 |
| WO | WO-2015029039 A1 | 3/2015 |
| WO | WO-2015069387 A1 | 5/2015 |
| WO | WO-2019157247 A1 | 8/2019 |
| WO | WO-2019157406 A1 | 8/2019 |
| WO | WO-2019157247 A9 | 4/2020 |

(56) References Cited

FOREIGN PATENT DOCUMENTS

| WO | WO-WO A9 2019157409 | 5/2020 |
|---|---|---|
| WO | WO-2021173775 A1 | 9/2021 |
| WO | WO-2021173791 A1 | 9/2021 |

OTHER PUBLICATIONS

"U.S. Appl. No. 16/803,612, Advisory Action dated Dec. 1, 2022", 3 pgs.
"U.S. Appl. No. 16/803,612, Examiner Interview Summary dated Nov. 8, 2022", 3 pgs.
"U.S. Appl. No. 16/803,612, Final Office Action dated Sep. 14, 2022", 34 pgs.
"U.S. Appl. No. 16/803,612, Non Final Office Action dated Dec. 28, 2022", 32 pgs.
"U.S. Appl. No. 16/803,612, Response filed Nov. 8, 2022 to Final Office Action dated Sep. 14, 2022", 18 pgs.
"U.S. Appl. No. 16/803,612, Response filed Dec. 9, 2022 to Advisory Action dated Dec. 1, 2022", 17 pgs.
"U.S. Appl. No. 16/803,649, Examiner Interview Summary dated Feb. 21, 2023", 2 pgs.
"U.S. Appl. No. 16/803,649, Examiner Interview Summary dated Oct. 5, 2022", 3 pgs.
"U.S. Appl. No. 16/803,649, Final Office Action dated Dec. 22, 2022", 17 pgs.
"U.S. Appl. No. 16/803,649, Response filed Feb. 21, 2023 to Final Office Action dated Dec. 22, 2022", 12 pgs.
"U.S. Appl. No. 16/803,649, Response filed Oct. 4, 2022 to Non Final Office Action dated Jul. 7, 2022", 15 pgs.
"International Application Serial No. PCT/US2021/019568, International Preliminary Report on Patentability dated Sep. 9, 2022", 7 pgs.
"International Application Serial No. PCT/US2021/019599, International Preliminary Report on Patentability dated Sep. 9, 2022", 7 pgs.
"Japanese Application Serial No. 2020-542770, Examiners Decision of Final Refusal dated Feb. 27, 2023", w/ English Translation, 7 pgs.
"Japanese Application Serial No. 2020-542770, Notification of Reasons for Refusal dated Nov. 14, 2022", w/ English translation, 14 pgs.
"Japanese Application Serial No. 2020-542770, Response filed Feb. 10, 2023 to Notification of Reasons for Refusal dated Nov. 14, 2022", with machine translation, 24 pgs.
"Japanese Application Serial No. 2020-542995, Notification of Reasons for Rejection dated Nov. 7, 2022", w/ English Translation, 9 pgs.
"Japanese Application Serial No. 2020-542995, Response filed Feb. 3, 2023 to Notification of Reasons for Rejection dated Nov. 7, 2022", with English claims, 10 pgs.
"International Application Serial No. PCT/US2015/045788, International Search Report dated Nov. 3, 2015", 3 pgs.
"International Application Serial No. PCT/US2015/045788, Written Opinion dated Nov. 3, 2015", 5 pgs.
"International Application Serial No. PCT/US2019/017153, International Search Report dated Apr. 30, 2019", 2 pgs.
"International Application Serial No. PCT/US2019/017153, Written Opinion dated 30, 2019", 6 pgs.
"U.S. Appl. No. 16/803,612, Examiner Interview Summary dated Mar. 28, 2023", 3 pgs.
"U.S. Appl. No. 16/803,612, Response filed Mar. 23, 2023 to Non Final Office Action dated Dec. 28, 2022", 14 pgs.
"U.S. Appl. No. 16/803,649, Advisory Action dated Mar. 24, 2023", 5 pgs.
"Indian Application Serial No. 202247046058, First Examination Report dated Apr. 11, 2023", 6 pgs.
U.S. Appl. No. 16/803,612, filed Feb. 27, 2020, Endoscope Unclogging Systems and Method.
U.S. Appl. No. 16/968,801, filed Aug. 10, 2020, System, Method and Computer-Readable Storage Device for Controlling Laser Light Source of Lithotripsy Device.
U.S. Appl. No. 16/803,649, filed Feb. 27, 2020, Suction and Irrigation Control System and Method.
"U.S. Appl. No. 16/803,612, Non Final Office Action dated Mar. 7, 2022", 38 pgs.
"U.S. Appl. No. 16/803,649, Response filed Apr. 14, 2022 to Restriction Requirement dated Feb. 16, 2022", 8 pgs.
"U.S. Appl. No. 16/803,649, Restriction Requirement dated Feb. 16, 2022", 6 pgs.
"European Application Serial No. 19750838.5, Response filed Apr. 28, 2022 to Extended European Search Report dated Oct. 1, 2021", 16 pgs.
"Korean Application Serial No. 10-2020-7026082, Voluntary Amendment Filed Jan. 11, 2022", w/English Claims, 15 pgs.
"U.S. Appl. No. 16/803,612, Examiner Interview Summary dated Jun. 3, 2022", 3 pgs.
"U.S. Appl. No. 16/803,612, Response filed May 31, 2022 to Non Final Office Action dated Mar. 7, 2022", 25 pgs.
"U.S. Appl. No. 16/803,649, Non Final Office Action dated Jul. 7, 2022", 15 pgs.
"European Application Serial No. 19750838.5, Response filed Apr. 28, 2022 to Communication pursuant to Rules 70(2) and 70a(2) EPC dated Oct. 19, 2021", 16 pgs.
"European Application Serial No. 19750915.1, Response filed Jun. 9, 2022 to Extended European Search Report dated Nov. 22, 2021", 10 pgs.
"European Application Serial No. 19750838.5, Extended European Search Report dated Oct. 1, 2021", 8 pgs.
"European Application Serial No. 19750838.5, Response filed Mar. 13, 2021", 17 pgs.
"European Application Serial No. 19750915.1, Response filed Mar. 16, 2021", 9 pgs.
"International Application Serial No. PCT/US2021/019568, International Search Report dated May 14, 2021", 4 pgs.
"International Application Serial No. PCT/US2021/019568, Written Opinion dated May 14, 2021", 5 pgs.
"International Application Serial No. PCT/US2021/019599, International Search Report dated May 19, 2021", 5 pgs.
"International Application Serial No. PCT/US2021/019599, Written Opinion dated May 19, 2021", 5 pgs.
"International Application Serial No. PCT/US2019/017391, International Preliminary Report on Patentability dated Aug. 20, 2020", 8 pgs.
"U.S. Appl. No. 16/803,612, Final Office Action dated Jul. 24, 2023", 35 pgs.
"U.S. Appl. No. 16/803,649, Non Final Office Action dated May 26, 2023", 22 pgs.
"U.S. Appl. No. 16/803,649, Response filed Aug. 28, 2023 to Non Final Office Action dated May 26, 2023", 13 pgs.
"U.S. Appl. No. 16/968,801, Restriction Requirement dated Aug. 3, 2023", 9 pgs.
"Japanese Application Serial No. 2020-542770, Response filed Jun. 27, 2023 to Examiners Decision of Final Refusal dated Feb. 27, 23", with machine translation, 23 pgs.
"Japanese Application Serial No. 2020-542995, Notification of Reasons for Refusal dated May 22, 2023", w/ English translation, 8 pgs.
"Japanese Application Serial No. 2020-542995, Response filed Sep. 7, 23 to Notification of Reasons for Refusal dated May 22, 2023", w/ english claims, 9 pgs.
"Japanese Application Serial No. 2022-551708, Notification of Reasons for Refusal dated Aug. 28, 2023", w/ English Translation, 9 pgs.
"U.S. Appl. No. 16/803,612, Advisory Action dated Oct. 5, 2023", 3 pgs.
"U.S. Appl. No. 16/803,612, Response filed Sep. 25, 23 to Final Office Action dated Jul. 24, 2023", 15 pgs.
"U.S. Appl. No. 16/803,612, Response filed Oct. 24, 2023 to Advisory Action dated Oct. 5, 2023", 14 pgs.
"U.S. Appl. No. 16/968,801, Response filed Oct. 3, 2023 to Restriction Requirement dated Aug. 3, 2023", 11 pgs.

(56) References Cited

OTHER PUBLICATIONS

"Canadian Application Serial No. 3,169,535, Examiners Rule 86(2) Requisition dated Sep. 29, 2023", 4 pgs.

"Canadian Application Serial No. 3,169,549, Examiners Rule 86(2) Report dated Sep. 29, 2023", 4 pgs.

"Indian Application Serial No. 202247046058, Response filed Oct. 4, 2023 to Office Action dated Apr. 11, 2023", 24 pgs.

"Japanese Application Serial No. 2022-551708, Response filed Oct. 13, 2023 to Notification of Reasons for Refusal dated Aug. 28, 2023", with English claims, 12 pgs.

"Mexican Application Serial No. MX/a/2020/008318, Office Action dated Aug. 31, 2023", with machine translation, 9 pgs.

"U.S. Appl. No. 16/803,612, Non Final Office Action dated Nov. 8, 2023", 26 pgs.

"U.S. Appl. No. 16/803,649, Final Office Action dated Dec. 13, 2023", 24 pgs.

"U.S. Appl. No. 16/968,801, Non Final Office Action dated Dec. 14, 2023", 16 pgs.

"Iteration", Merriam-Webster.com Dictionary, Merriam-Webster, [Online] Retrieved from the internet: <https://www.merriam-webster.com/dictionary/iteration>, (Dec. 2023), 1 pg.

"Australian Application Serial No. 2019216954, Response filed Jan. 8, 24 to First or Subsequent Examiner Report mailed Oct. 23, 23", 22 pgs.

"Australian Application Serial No. 2019217992, First Examination Report mailed Nov. 22, 23", 4 pgs.

"Chinese Application Serial No. 201980012090.7, Office Action mailed Nov. 3, 23", w/English Translation, 25 pgs.

"Chinese Application Serial No. 201980012090.7, Response filed Dec. 27, 23 to Office Action mailed Nov. 3, 23", with English claims, 16 pgs.

"Japanese Application Serial No. 2022-551714, Response filed Dec. 18, 23 to Notification of Reasons for Refusal mailed Oct. 23, 23", with English claims, 10 pgs.

"Japanese Application Serial No. 2023-105314, Voluntary Amendment mailed Dec. 15, 23", with machine translation, 9 pgs.

"Korean Application Serial No. 10-2020-7026082, Notice of Preliminary Rejection mailed Dec. 21, 23", with machine translation, 6 pgs.

"Mexican Application Serial No. MX/a/2020/008318, Response filed Nov. 16, 23 to Office Action mailed Aug. 31, 23", with machine translation, 23 pgs.

"Canadian Application Serial No. 3,169,535, Response filed Jan. 25, 2024 to Examiners Rule 86(2) Requisition mailed Sep. 29, 2023", 16 pgs.

"Canadian Application Serial No. 3,169,549, Response filed Jan. 29, 2024 to Examiners Rule 86(2) Report mailed Sep. 29, 2023", 19 pgs.

"Chinese Application Serial No. 201980012086.0, First Office Action mailed Jan. 15, 2024", with English translation, 21 pgs.

"European Application Serial No. 19750838.5, Communication Pursuant to Article 94(3) EPC mailed Feb. 8, 2024", 3 pgs.

"Japanese Application Serial No. 2022-551708, Examiners Decision of Final Refusal mailed Jan. 15, 2024", W/English Translation, 6 pgs.

"Korean Application Serial No. 2020-7025950, Notice of Preliminary Rejection mailed Jan. 30, 2024", with machine translation, 16 pgs.

"U.S. Appl. No. 16/803,612, Examiner Interview Summary mailed Feb. 8, 2024", 3 pgs.

"U.S. Appl. No. 16/803,612, Response filed Feb. 5, 2024 to Non Final Office Action mailed Nov. 8, 2023", 15 pgs.

"U.S. Appl. No. 16/803,649, Advisory Action mailed Feb. 13, 2024", 3 pgs.

"U.S. Appl. No. 16/803,649, Examiner Interview Summary mailed Feb. 6, 2024", 3 pgs.

"U.S. Appl. No. 16/803,649, Response filed Feb. 2, 2024 to Final Office Action mailed Dec. 13, 2023", 13 pgs.

\* cited by examiner

MEDICAL LASER APPARATUS AND SYSTEM

CROSS-REFERENCE TO RELATED APPLICATION

This application is a U.S. National Stage Filing under 35 U.S.C. 371 from International Application No. PCT/US2019/017153, filed on Feb. 8, 2019, and published as WO 2019/157247 on Aug. 15, 2019, which claims the benefit of U.S. Provisional Application No. 62/628,513 filed on Feb. 9, 2018, the entire contents of which are incorporated herein by reference in their entireties.

BACKGROUND

1. Field

The invention relates generally to a medical laser apparatus and system and more particularly to a medical laser apparatus and system for use with an endoscope system having two or more illumination modes.

2. Prior Art

Medical lasers have been utilized in a variety of treatment procedures including, for example, various endoscopic procedures. Generally, these procedures require precisely controlled delivery of energy in order to successfully accomplish the desired procedure.

Generally, a surgical probe is utilized to deliver laser energy to a target tissue. The surgical probe generally comprises an energy guide, such as an optical fiber, coupled to an energy source, such as a laser, wherein the probe can be positioned such that the tip of the probe is positioned adjacent to the target tissue. Laser energy is directed out of the tip of the optical fiber onto desired portions of the target tissue. The laser optical fiber coupled to the laser source is required to be somewhat flexible such that the optical fiber can be manipulated. The laser system can include, for example, a Thulium Fiber Laser, which is used to generate the laser light for delivery through the optical fiber to the target tissue. The laser is capable of being operated in different treatment modes, such as a cutting (ablation) mode and a coagulation (hemostasis) mode.

The medical professional performing the particular procedure manipulates the optical fiber into position near the targeted tissue and sets the laser power and mode for various treatments, which may require different power and mode settings depending on the treatment, such as vaporization mode or coagulation mode.

The laser beam used for treating tissue is typically invisible to the human eye and to standard image sensors. Therefore, another illumination source can be used to generate a visible aiming beam. With the use of the aiming beam, an aiming beam spot can appear in the images formed when an endoscope is being used to view the target area.

Also, an endoscopic video imaging system has functions to assist the early detection of minute lesions, such as cancer and preoperative accurate diagnosis of diseased areas. The system incorporates specific light imaging functions using specific light spectra in addition to normal light imaging. The endoscopic video imaging system can have at least two illumination modes, white light (normal light) illumination and a specific light illumination mode. The endoscope also has an illumination mode switching function that changes from the white light mode to specific light illumination mode or from specific light illumination mode to the white light mode.

SUMMARY

Accordingly, a medical laser apparatus is provided. The medical laser apparatus comprising: an energy guide; a first energy source configured to generate energy for treating a target tissue through the energy guide; a second energy source configured to emit first and second aiming beams to a target tissue through the energy guide, the second aiming beam having at least one characteristic different from the first aiming beam; and a controller comprising hardware, the controller being configured to: receive a signal indicating an illumination mode from at least two illumination modes used by an endoscope to illuminate the target tissue; and control the second energy source to output the first or second aiming beam based on the indicated illumination mode.

Wherein when a white light illumination mode is indicated, the controller can control the second energy source to emit the first aiming beam having a wavelength in the range of 500 nm to 550 nm.

Wherein when a special light illumination mode is indicated, the controller can control the second energy source to emit the first aiming beam having a wavelength in the range of 635 nm to 690 nm. The special light mode can be one of a narrow band imaging mode, an auto fluorescence imaging mode or an infrared imaging mode.

The controller can be further configured to receive a signal indicating whether a spot caused by the first or second aiming beam can be identified in an image from the endoscope. When the spot cannot be identified in the image, the controller can be further configured to switch one of the first or second aiming beams to an other of the first or second aiming beams. The controller can be further configured to receive a signal indicating whether a spot caused by the other of the first or second aiming beam can be identified in the image from the endoscope. When the spot from the other of the first or second aiming beam cannot be identified in the image, the controller can be configured to control the first energy source to prohibit the first energy source from generating energy for treating the target tissue.

The at least one characteristic can be selected from a group consisting of wavelength, power level and emitting pattern.

The energy guide can be a laser fiber.

The first energy source can be a treatment laser beam.

Also provided is an endoscope controller comprising hardware, where the endoscope controller is for use with an endoscope. The endoscope controller being configured to: output a first signal indicating an illumination mode of the endoscope; detect whether a spot from an aiming beam generated by an aiming beam energy source is visible in an image captured by an image sensor in the endoscope; and outputting a second signal based on the detection.

The second signal can be output only where the spot cannot be detected in the image.

The aiming beam can be a first aiming beam; and where the spot cannot be detected in the image, the second signal can instruct a laser apparatus to one of change the first aiming beam to a second aiming beam having at least one characteristic different from the first aiming beam.

Still further provided is a medical system comprising: a medical laser apparatus, comprising: an energy guide; a first energy source configured to generate energy for treating a target tissue through the energy guide; a second energy source configured to emit first and second aiming beams to a target tissue through the energy guide, the second aiming beam having at least one characteristic different from the first aiming beam; and a first controller comprising hardware, the first controller being configured to: receive a first signal indicating an illumination mode from at least two illumination modes used by an endoscope to illuminate the target tissue; control the second energy source to output the first or second aiming beam based on the indicated illumination mode; and a second controller comprising hardware, the second controller being for use with an endoscope, the second controller being configured to: output the first signal to the first controller indicating the illumination mode from the at least two illumination modes used by the endoscope.

When a white light illumination mode is indicated, the first controller can control the second energy source to emit the first aiming beam having a wavelength in the range of 500 nm to 550 nm.

When a special light illumination mode is indicated, the first controller can control the second energy source to emit the first aiming beam having a wavelength in the range of 635 nm to 690 nm. The special light mode can be one of a narrow band imaging mode, an auto fluorescence imaging mode or an infrared imaging mode.

The second controller can be further configured to: output a second signal indicating whether a spot caused by the first or second aiming beam can be identified in an image from the endoscope; and the first controller can be further configured to: receive the second signal; and when the spot cannot be identified in the image, switch one of the first or second aiming beams to an other of the first or second aiming beams.

The second controller can be further configured to: output a second signal indicating whether a spot caused by the first or second aiming beam can be identified in an image from the endoscope; and the first controller can be further configured to: receive the second signal; and when the spot from the other of the first or second aiming beam cannot be identified in the image, control the first energy source to prohibit the first energy source from generating energy for treating the target tissue.

The at least one characteristic can be selected from a group consisting of wavelength, power level and emitting pattern.

The energy guide can be a laser fiber.

The first energy source can be a treatment laser beam.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
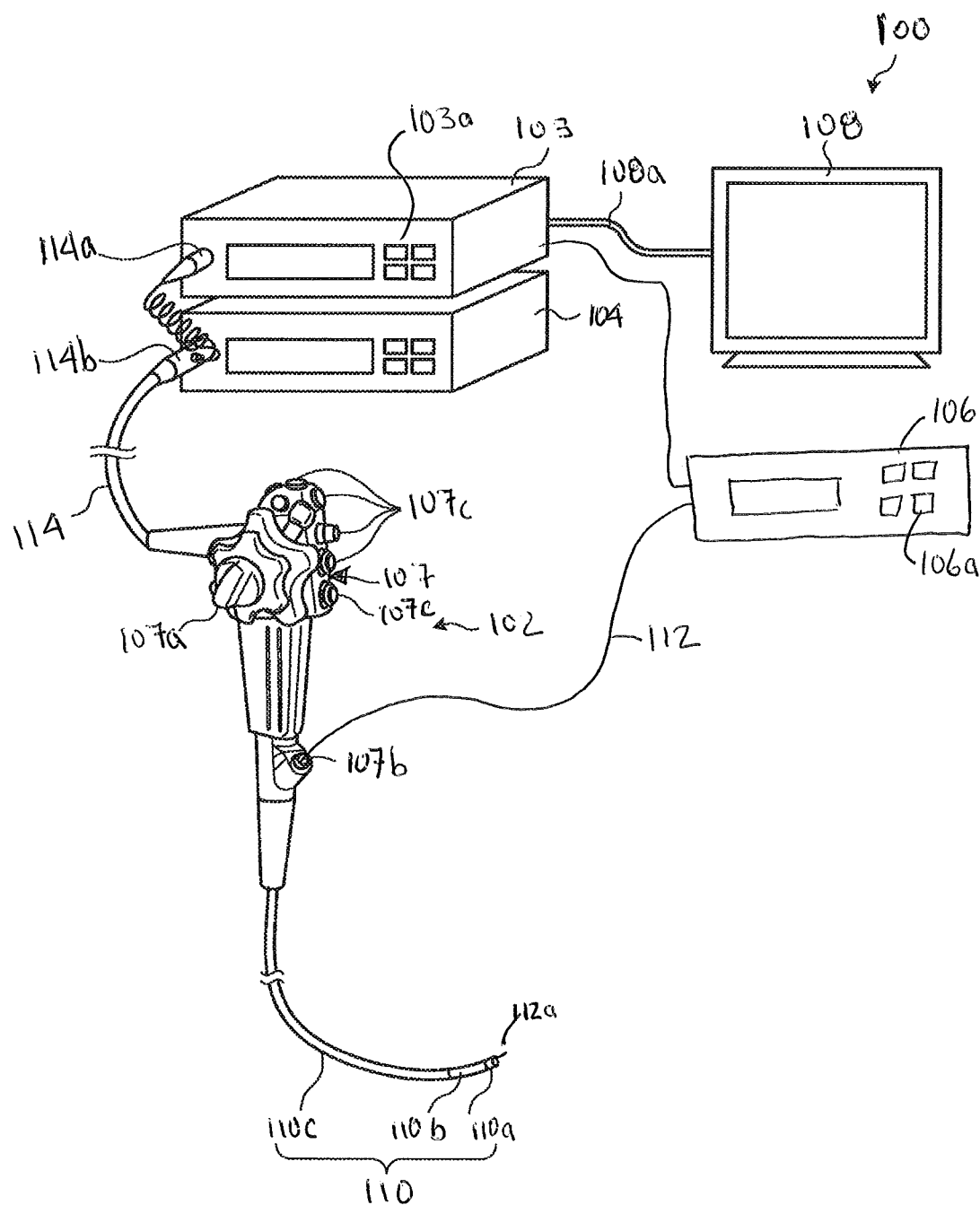
FIG. 1 illustrates a medical system having an endoscope, laser apparatus, endoscope processor and endoscope light source.

Referring now to FIG. 1, the same illustrates an overall configuration of a medical system 100 having an endoscope 102, an endoscope processor 103, a light source 104, a laser apparatus 106 and a display 108. As illustrated in FIG. 1, the endoscope 102 includes an insertion section 110 configured to be inserted into a subject that images the inside of the subject and generates an image signal of the inside of the subject, the endoscope processor 103 that performs predetermined image processing on the image signal captured by the endoscope 102 and controls at least parts of medical system 100, the light source 104 that generates illumination light of the endoscope 102 having at least two illumination modes, the laser apparatus 106 having a first energy source for generating energy for treating a target tissue through an energy guide 112 and a second energy source configured to emit two or more aiming beams to a target tissue through the energy guide 112, and the display device 108 that displays the aiming beam and an image of the image signal having been subject to the image processing performed by the endoscope processor 103.

The endoscope 102 includes the insertion portion 110 to be inserted into the subject, an operating unit 107 to be held by an operator, which is on a proximal end portion side of the insertion portion 110, and a flexible universal cord 114 extended from the operating unit 107. Although FIG. 1 illustrates a Gastrointestinal (GI) endoscope, the apparatus and systems disclosed herein are not limited to a GI endoscope and also have particular utility for use with other types of endoscopes, such as ureteroscope or cystoscope or those used for a other treatment procedures.

The insertion portion 110 is formed using a lighting fiber (light guide), an electric cable, an optical fiber, and the like. The insertion portion 110 includes a distal end portion 110a incorporating an imaging unit to be described later, a bendable bend portion 110b including a plurality of bend pieces, and a flexible tube portion 110c provided on a proximal end portion side of the bend portion 110b, which is flexible. The distal end portion 110a is provided with an illumination light guide 120 (see FIG. 2) that illuminates the inside of the subject via an illumination lens 122 (see FIG. 2), an observation unit, including an image sensor, such as a CCD or CMOS and an objective lens system 118 (see FIG. 2) that images the inside of the subject, an insertion port 107b that communicates with a treatment tool channel 102a (see FIG. 2), and an air/water supply nozzle (not illustrated).

The operating unit 107 includes a bending knob 107a for bending the bend portion 110b in the up and down direction and the right and left direction, the treatment tool insertion port 107b through which a treatment tool, such as medical forceps or the energy guide 112 is inserted into a body cavity of the subject, and a plurality of switches 107c for operating a peripheral device such as the endoscope processor 103, the light source device 104, an air supply device, a water supply device, and a gas supply device. The treatment tool, such as the energy guide 112 can be inserted from the treatment tool insertion port 107b and through the channel 102a such that a distal end thereof is exposed from an opening 102b (see FIG. 2) of the channel 102a at the distal end of the insertion portion 110.

The universal cord 114 includes a lighting fiber, a cable, and the like. The universal cord 114 is branched at the proximal end thereof. One end of the branched ends is a connector 114a, and the other proximal end of the branched ends is a connector 114b. The connector 114a is attachable/detachable to/from a connector of the endoscope processor 103. The connector 114b is attachable/detachable to/from the light source 104. The universal cord 114 propagates the illumination light emitted from the light source 104 to the distal end portion 110a via the connector 114b and the light guide 120 (see FIG. 2). Further, the universal cord 114 transmits an image signal captured by the image sensor 116 (see FIG. 2) to be described later to the endoscope processor 103 via a signal line 124 (see FIG. 2) in the cable and via the connector 114a.

The endoscope processor 103 executes predetermined image processing on the image signal output from the connector 114a, and controls at least part of the components making up the medical system 100.

The light source 104 includes one or more light sources that emit light having one or more illumination characteristics, referred to as illumination modes, a condenser lens, and the like. Such light sources can be, for example, a Xenon lamp, an LED (Light-Emitting Diode), an LD (Laser Diode), or any combination thereof. Under the control of the endoscope processor 103, the light source 104 emits light from the one or more light sources thereof, and supplies the light to the endoscope 102 connected via the connector 114b and the light guide of the universal cord 114 as illumination light for the inside of the subject as an object. The illumination modes can be a white light illumination mode or a special light illumination mode, such as a narrow band imaging mode, an auto fluorescence imaging mode or an infrared imaging mode. A special light illumination can concentrate and intensify specific wavelengths of light, for example, resulting in a better visualization of a superficial microvessel and mucosal surface structures to enhance the subtle contrast of the irregularities of the mucosa.

The display 108 includes, for example, a liquid crystal display, an organic electro luminescence (EL) display, or the like. The display 108 displays various kinds of information including the image having been subject to predetermined image processing by the information processing apparatus 103 via a video cable 108a. This allows an operator to observe and determine behavior of the desired position inside the subject by operating the endoscope 102 while watching the image (in-vivo image) displayed by the display 108.

Figure 2:
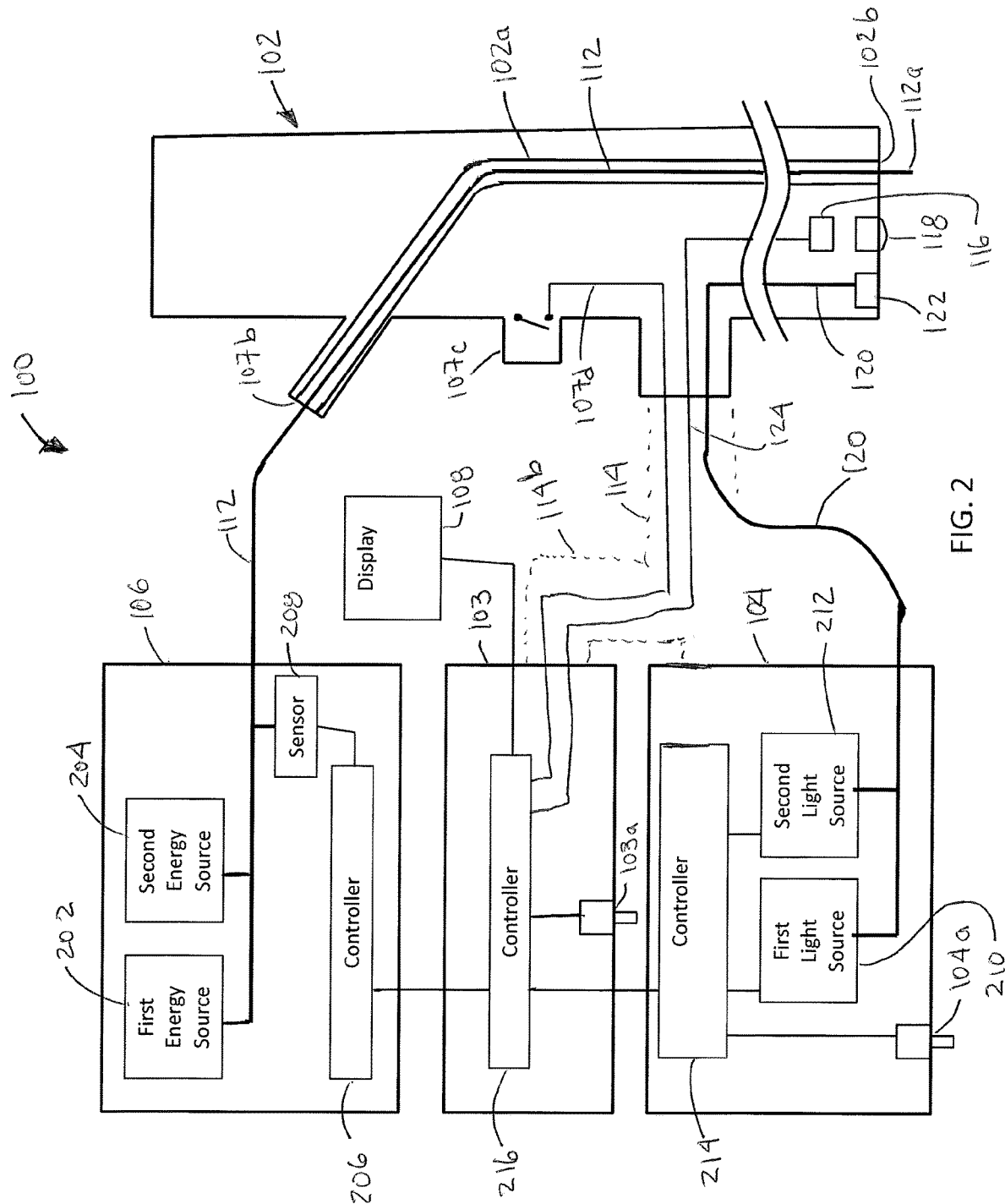
FIG. 2 illustrates a schematic view of the medical system of FIG. 1 including a distal-end of the endoscope of FIG. 1.

Referring now to FIG. 2, the medical system 100 of FIG. 1 is shown schematically. The laser apparatus 106 is for use with the energy guide 112, such as a laser fiber. The energy guide is disposed in the channel 102a through the treatment insertion port 107b and includes a distal end 112a that extends distally from the distal end opening 102b of the channel 102a so as to be configured to direct treatment energy to the target tissue. A proximal end of the energy guide 112 is operatively connected to the laser apparatus 106.

The laser apparatus 106 includes two or more energy sources for generating laser energy coupled to the proximal end of the energy guide 112. Such energy sources can be selectable by a user by an input, such as a button 106a on the laser apparatus 106 or a foot switch (not shown), through software or a user interface on the display 108 or other inputs, manual or automatic as are known in the art. A first energy source 202 is optically coupled to the energy guide 112 and can be configured to generate energy for treating the target tissue through the energy guide 112. For example, the first energy source 202 can be a thulium laser, used to generate laser light for delivery through the light guide 112 to the target tissue to operate in different treatment modes, such as a cutting (ablation) mode and a coagulation (hemostasis) mode. Other energy sources known in the art for such treatment of tissue, or any other treatment modes, can also be used for the first energy source 202, such as Ho:YAG, Nd:YAG and $CO_2$ as well as others known in the art.

The two or more energy sources can also include a second energy source 204 also optically coupled to the energy guide 112 and configured to emit at least two aiming beams to the target tissue through the energy guide 112, where the first aiming beam has at least one characteristic different from the second aiming beam. Such differing characteristics can be wavelength, power level and/or emitting pattern. For example, the first aiming beam can have a wavelength in the range of 500 nm to 550 nm while the second aiming beam can have a wavelength in the range of 635 nm to 690 nm. The characteristics of the different aiming beams can be selected based on the visibility of the aiming beams in the image processed by the endoscope processor 103 and displayed on the display 108 under certain illumination modes provided by the light source 104.

The laser apparatus 106 further includes a controller 206 comprising hardware, such as a CPU, that controls the operation of the laser apparatus 106 including the first and second energy sources 202, 204. The laser apparatus 106 can further include a sensor 208 operatively coupled to the energy guide 112 and under the control of the controller 206. The sensor 208 is configured, as known in the art, to detect reflected light through the energy guide 112 from the distal end 112a of the energy guide 112 and back to the sensor 208 such that the sensor 208 can determine an illumination mode output to the light guide 120 from the light source 104. That is, such sensor 208 detects the illumination mode being used to illuminate the target tissue. Such reflected light detection can be similar to that described in U.S. Pat. No. 5,860,972 issued on Jan. 19, 1999, the contents of which is incorporated herein by reference.

The light source 104 includes one or more light sources, such as a first light source 210 and a second light source 212 under the control of a controller 214. The light sources 210, 212 can be selected by a user through an input, such as a button 104a on the light source 104 or a foot switch (not shown), through software or a user interface on the display 108 or other inputs, manual or automatic as are known in the art. The first and second light sources 210, 212 are optically coupled to the light guide 120 to provide different illumination modes, as described above, to the light guide 120. Although a different light source is shown for each illumination mode, a single light source can be provided to produce illumination modes having different characteristics through the use of filters, lens and the like.

The endoscope processor 103 also includes a controller 216 comprising hardware, such as a CPU, for control of the endoscope 102, display 108, light source 104 and/or laser apparatus 106. The controller 216, as discussed above, receives a signal from the image sensor 116 through line 124 in the universal cord 114 to process the same so as to generate an image/video for viewing on the display 108. Such image includes not only the target area of the tissue to be treated under the illumination of the light source 104 but also an aiming beam generated by the laser apparatus 106 when the first energy source 202 is active and the energy guide 112 is being used to treat the target tissue. The endoscope processor 103 includes one or more inputs, such as a button 103a on the endoscope processor 103 or a foot switch (not shown), through software or a user interface on the display 108 or other inputs, manual or automatic as are known in the art.

Figure 3:
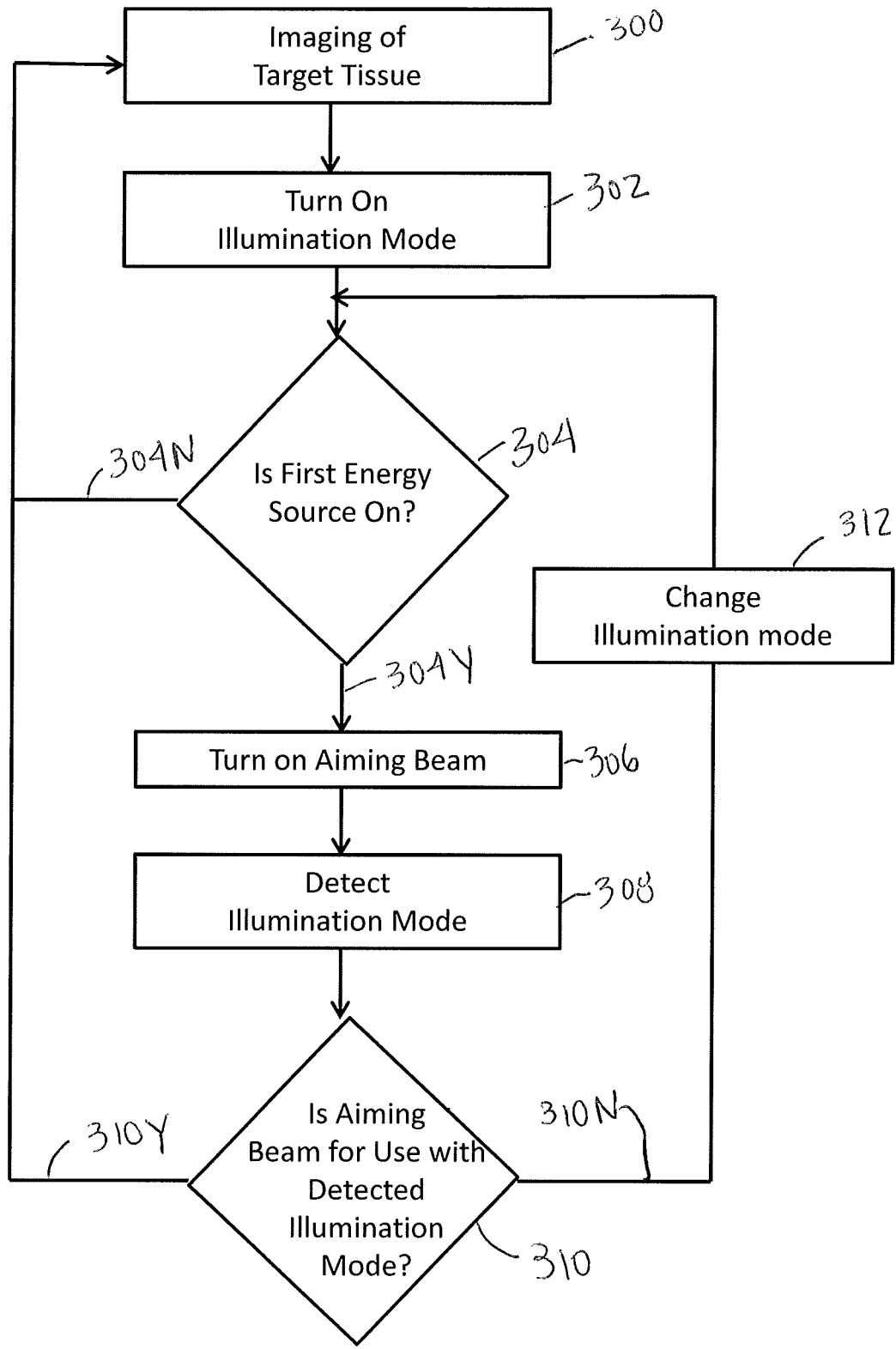
FIG. 3 illustrates a flow chart of a first method of operation of the medical system of FIG. 1.

A use of the medical system 100 of FIG. 1 will now be described with regard to the flow chart illustrated in FIG. 3. After insertion of the endoscope 102 to the target tissue site, the user views the target tissue on the display 108 at 300. Such viewing of the target tissue is with an illumination mode set at 302 and output by one of the light sources 210, 212 of the light source 104. Such illumination mode can be set by selection by the user by any means known in the art or automatically provided by a determination made by either of controllers 214, 216 based on predetermined criteria.

A determination is made at 304 by the controller 206 as to whether the first energy source 202 is activated (on) and delivering treatment energy to the energy guide 112. Where it is determined that the first energy source 202 is not delivering treatment energy to the energy guide 112, the controller 206, at 304N, does not activate the second energy source 204 to generate an aiming beam. Where it is determined that the first energy source 202 is delivering treatment energy to the energy guide 112, the controller 206, at 304Y, activates the second energy source 204, at 306, to generate one of the first or second aiming beams.

At 308, the controller 206 determines the illumination mode from the illumination modes used by the endoscope to illuminate the target tissue, such as receiving a signal indicating the type of illumination mode being used. The illumination mode signal provided to the controller 206 can be a manual input from the user at input 104a of the light source 104 to direct the light source controller 214 to output a signal to the controller 216 of the endoscope processor 103, which in turn outputs a signal to the laser apparatus controller 206. Such manual input can also be from the input, such as button 103a, of the endoscope processor 103. The light source controller 214 can also directly output a signal indicating the illumination mode to the laser apparatus controller 206. The input can also be via a button 107c on the endoscope through signal line 107d to the controller 216 of the endoscope processor 103, which is in turn relayed to the controller 206 of the laser apparatus. The controller 206 of the laser apparatus 106 can also receive a signal indicative of the illumination mode used by the endoscope from the sensor 208, which detects the illumination being used by reflected light through the energy guide 112 and the controller 206 processes such detection and determines the illumination mode based on the output from the sensor 208. Furthermore, the controller 216 of the endoscope processor 103 can analyze the image signal from the image sensor 116 and determine an illumination mode based on such image signal and output such determination to the controller 206 of the laser apparatus 106. Other sensors (not shown) may also be employed for determination of the illumination mode being used by the endoscope, such as at the distal end of the endoscope 102 or in the endoscope processor 103.

At 310, a determination is made as to whether the aiming beam is appropriate for the determined illumination mode. Such determination can be based on historical data reflected in a look up table (LUT) operatively connected to the controller 206, where the LUT corresponds illumination mode to aiming beam characteristic. Such LUT can store data of illumination modes (or the wavelength of the illumination light) and a corresponding wavelength of aiming beam for use with such illumination mode or wavelength of such illumination mode. Where it is determined that the aiming beam being used is appropriate for use with the illumination mode being used, no change is required in the aiming beam being used and the process continues at 310Y to image the target tissue until the determination is made at 310N that the aiming beam being used is not appropriate for use with the illumination mode being used. Such determination can be made upon predetermined intervals or upon an occurrence of a predetermined event, such as the first energy source being turned off and then again on.

However, where it is determined, at 310N, that the aiming beam being used is not appropriate for use with the illumination mode being used, the second energy source 204 is controlled to change the aiming beam at 312 based on the indicated illumination mode. For example, when a white light illumination mode is determined, the controller 206 can control the second energy source 204 to emit a first aiming beam having a wavelength in the range of 500 nm to 550 nm. Alternatively, where a special light illumination mode is determined, the controller 206 can control the second energy source 204 to emit the second aiming beam having a wavelength in the range of 635 nm to 690 nm. As discussed above, the special light mode can be, for example, one of a narrow band imaging mode, an auto fluorescence imaging mode or an infrared imaging mode.

Figure 4:
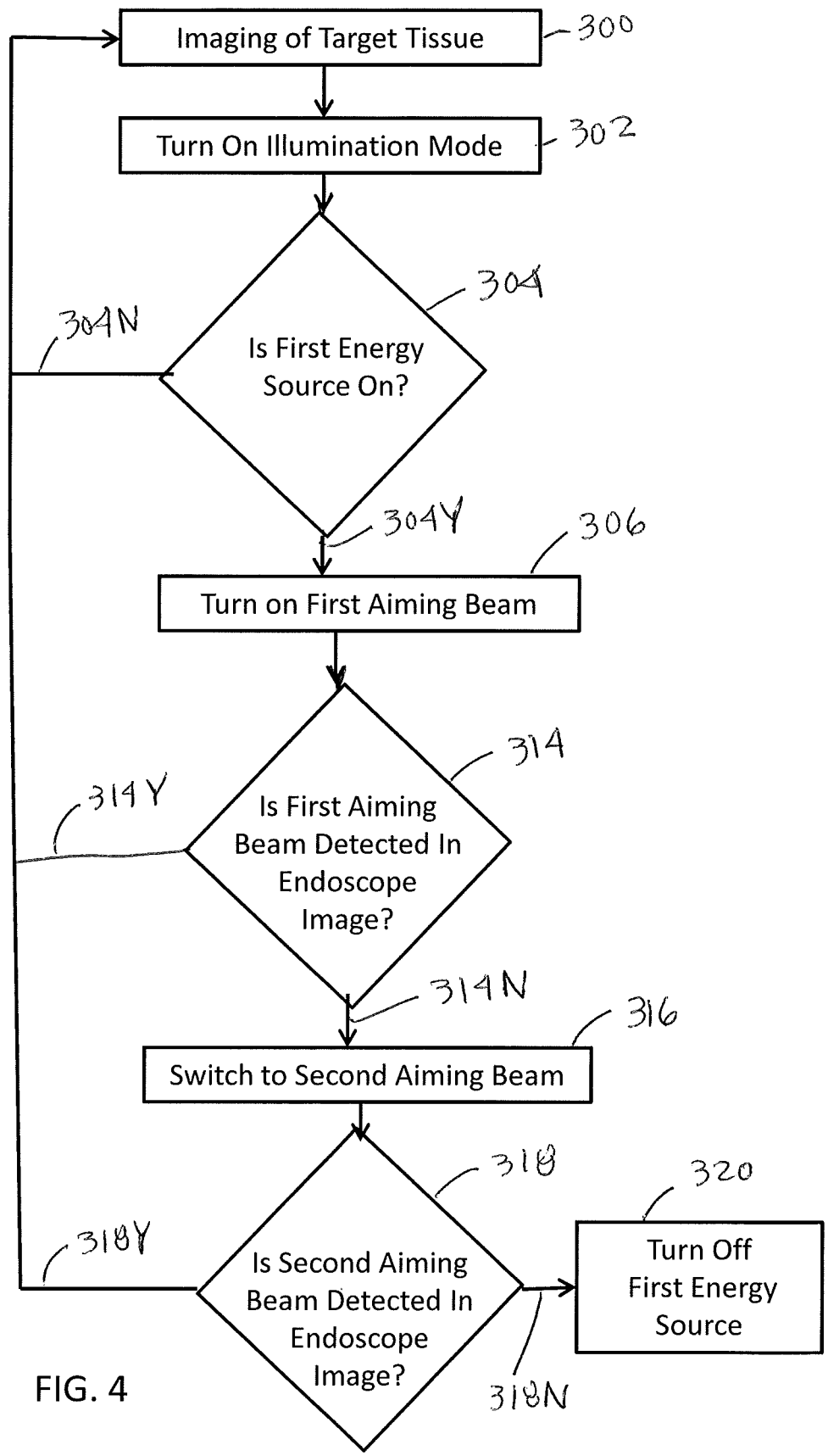
FIG. 4 illustrates a flow chart of a second method of operation of the medical system of FIG. 1.

Another use of the medical system 100 of FIG. 1 will now be described with regard to the flow chart illustrated in FIG. 4, in which 300, 302, 304 and 306 are substantially as described above. Where one of the aiming beams, such as the first or second aiming beams is activated by the laser apparatus 106, a determination is made at 314 as to whether a spot caused by the first or second aiming beam can be identified in an image from the endoscope 102. That is, the controller 216 analyzes the image signal from the image sensor 116 to determine if the aiming beam spot being used is visible in the image of the target tissue. Such determination of a spot in image data is well known in the art, such as by pixel comparison to determine a disparity (a discontinuity) in pixel data in an area of the image corresponding to an expected size and/or shape of the spot. Furthermore, such determination may consider the spot to not be visible if a spot is detected but the disparity is below some predetermined threshold where a user would have trouble identifying the spot clearly from the image.

Where the spot is detected, or is sufficiently detected in the image, the imaging, illumination and display of the image and spot continues, at 314Y, until such determination changes or the laser apparatus no longer activates the first energy source 202. Where the spot cannot be detected or not sufficiently detected in the image at 314N, the controller 216 outputs a signal, at 316, to the laser apparatus controller 206 to switch to a different one of the first or second aiming beams.

A similar determination is made by the controller 216 at 318 to determine whether a spot caused by the different one of the first or second aiming beams can be identified in the image from the endoscope 102. Where the spot is detected, or is sufficiently detected in the image at 318Y, the imaging, illumination and display of the image and spot continues until such determination changes or the laser apparatus no longer activates the first energy source 202. Where the spot cannot be detected or not sufficiently detected in the image at 318N, as a safety measure, the controller can output a signal to the laser apparatus controller 206 to control the first energy source to prohibit the first energy source from generating energy for treating the target tissue at 320.

Although described with regard to a flexible endoscope, the above apparatus and methods also have utility for rigid type endoscopes. In addition, although the laser apparatus 106 is described as a separate device, the features thereof can be incorporated into one or both of the light source and endoscope processor, in which a common controller can be used to make the determinations and control indicated herein.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A medical laser apparatus, comprising:
an energy guide;
a first energy source configured to generate energy for treating a target tissue through the energy guide;
a light source having at least two illumination modes for providing illumination to the target tissue;
a second energy source, different from the light source, configured to emit first and second aiming beams to a target tissue through the energy guide, the second aiming beam having at least one characteristic different from the first aiming beam; and
a controller comprising hardware, the controller being configured to:
receive a signal indicating one of the at least two illumination modes currently illuminating the target tissue;
select an aiming beam from the first and second aiming beams based on the illumination mode currently illuminating the target tissue; and
control the second energy source to emit the selected aiming beam to the target tissue.

2. The medical laser apparatus according to claim 1, wherein when a white light illumination mode is indicated, the controller controls the second energy source to emit the first aiming beam having a wavelength in a range of 500 nm to 550 nm.

3. The medical laser apparatus according to claim 1, wherein when a special light illumination mode is indicated, the controller controls the second energy source to emit the second aiming beam having a wavelength in a range of 635 nm to 690 nm.

4. The medical laser apparatus according to claim 3, wherein the special light mode is one of a narrow band imaging mode, an auto fluorescence imaging mode or an infrared imaging mode.

5. The medical laser apparatus according to claim 1, wherein the controller is further configured to receive a signal indicating whether a spot caused by the first or second aiming beam can be identified in an image of the target tissue.

6. The medical laser apparatus according to claim 5, wherein, when the spot cannot be identified in the image, the controller being further configured to switch one of the first or second aiming beams to another of the first or second aiming beams.

7. The medical laser apparatus according to claim 6, wherein the controller is further configured to receive a signal indicating whether a spot caused by the other of the first or second aiming beam can be identified in the image of the target tissue.

8. The medical laser apparatus according to claim 7, wherein, when the spot from the other of the first or second aiming beam cannot be identified in the image, the controller is configured to control the first energy source to prohibit the first energy source from generating energy for treating the target tissue.

9. The medical laser apparatus according to claim 1, wherein the at least one characteristic is selected from a group consisting of wavelength, power level and emitting pattern.

10. The medical laser apparatus according to claim 1, wherein the energy guide is a laser fiber.

11. The medical laser apparatus according to claim 1, wherein the first energy source is a treatment laser beam.

12. An endoscope controller comprising hardware, the endoscope controller being for use with an endoscope, the endoscope controller being configured to:
output a first signal indicating an illumination mode of the endoscope currently illuminating a target tissue;
based on the illumination mode, select from a plurality of aiming beams generated by an aiming beam energy source an aiming beam to emit to the target tissue;
detect whether a spot from the selected aiming beam is visible in an image captured by an image sensor in the endoscope; and
outputting a second signal based on the detection.

13. The endoscope controller of claim 12, wherein the second signal is output only where the spot cannot be detected in the image.

14. The endoscope controller of claim 12, wherein:
the aiming beam is a first aiming beam; and
where the spot cannot be detected in the image, the second signal instructs a laser apparatus to one of change the first aiming beam to a second aiming beam having at least one characteristic different from the first aiming beam.

15. A medical system comprising:
a medical laser apparatus, comprising:
an energy guide;
a first energy source configured to generate energy for treating a target tissue through the energy guide;
a second energy source configured to emit first and second aiming beams to a target tissue through the energy guide, the second aiming beam having at least one characteristic different from the first aiming beam;
a first controller comprising hardware, the first controller being configured to:
receive a first signal indicating an illumination mode from at least two illumination modes used by an endoscope to illuminate the target tissue;
select an aiming beam from the first and second aiming beams based on the illumination mode currently illuminating the target tissue; and
control the second energy source to emit the selected aiming beam to the target tissue; and
a second controller comprising hardware, the second controller being for use with an endoscope, the second controller being configured to:
output the first signal to the first controller indicating the illumination mode from the at least two illumination modes used by the endoscope.

16. The medical system of claim 15, wherein when a white light illumination mode is indicated, the first controller controls the second energy source to emit the first aiming beam having a wavelength in a range of 500 nm to 550 nm.

17. The medical system according to claim 15, wherein when a special light illumination mode is indicated, the first controller controls the second energy source to emit the first aiming beam having a wavelength in a range of 635 nm to 690 nm.

18. The medical system according to claim 17, wherein the special light mode is one of a narrow band imaging mode, an auto fluorescence imaging mode or an infrared imaging mode.

19. The medical system according to claim 15, wherein:
the second controller is further configured to:

output a second signal indicating whether a spot caused by the first or second aiming beam can be identified in an image from the endoscope; and the first controller is further configured to:

receive the second signal; and when the spot cannot be identified in the image, switch one of the first or second aiming beams to an other of the first or second aiming beams.

20. The medical system according to claim 15, wherein:

the second controller is further configured to:

output a second signal indicating whether a spot caused by the first or second aiming beam can be identified in an image from the endoscope; and the first controller is further configured to:

receive the second signal; and when the spot from the other of the first or second aiming beam cannot be identified in the image, control the first energy source to prohibit the first energy source from generating energy for treating the target tissue.

21. The medical system according to claim 15, wherein the at least one characteristic is selected from a group consisting of wavelength, power level and emitting pattern.

22. The medical system according to claim 15, wherein the energy guide is a laser fiber.

23. The medical system according to claim 15, wherein the first energy source is a treatment laser beam.

* * * * *